United States Patent [19]
Takeda et al.

[11] Patent Number: 6,043,050
[45] Date of Patent: Mar. 28, 2000

[54] BIOLOGICAL PROCESS FOR PRODUCING STEROIDS HYDROXYLATED AT THE 25-POSITION

[75] Inventors: Koji Takeda, Iwata; Tadashi Terasawa, Fujisawa; Kazuyuki Dobashi, Hadano; Takeo Yoshioka, Ayase, all of Japan

[73] Assignees: Mercian Corporation; Chugai Seiyaku Kabushiki Kaisha, both of Tokyo, Japan

[21] Appl. No.: 09/219,515

[22] Filed: Dec. 23, 1998

Related U.S. Application Data

[63] Continuation of application No. PCT/JP97/01909, Jun. 5, 1997.

[30] Foreign Application Priority Data

Jun. 27, 1996 [JP] Japan .................................. 8-166968

[51] Int. Cl.⁷ ..................................................... C12P 33/06
[52] U.S. Cl. ................................................................ 435/58
[58] Field of Search .................................................. 435/58

[56] References Cited

PUBLICATIONS

Abstract of Japanese Patent 7123997 A, 1995.

*Primary Examiner*—Jose' G. Dees
*Assistant Examiner*—Barbara Badio
*Attorney, Agent, or Firm*—Burns, Doane, Swecker & Mathis, LLP

[57] ABSTRACT

A biological process for producing steroids hydroxylated at the 25-position thereof comprises adding steroids (excluding cholesterol) to the cells or culture liquid of a microorganism of the genus Amycolata or Sphingomonas capable of hydroxylating the steroids at the 25-position thereof to convert a hydrogen atom bonded to a carbon atom at the 25-position of each steroid into hydroxyl group. By this process, steroids(other than cholesterol) can be biologically hydroxylated at the 25-position by using microorganisms other than those of the genus Streptomyces.

26 Claims, No Drawings

BIOLOGICAL PROCESS FOR PRODUCING STEROIDS HYDROXYLATED AT THE 25-POSITION

This is a continuation of international Application PCT/JP97/01909, having an international filing date of Jun. 5, 1997.

TECHNICAL FIELD

The present invention relates to a process for biologically hydroxylating the 25-position of steroids other than cholesterol.

BACKGROUND OF THE INVENTION

For the biological hydroxylation of steroids at the 25-position, there is already known a process wherein microorganisms of the genus Streptomyces capable of hydroxylating steroids at the 25-position thereof are used [Japanese Patent Unexamined Published Application (hereinafter referred to as "J. P. KOKAI") No. Hei 7-123997]. Concretely, Streptomyces sp. HB-103 is mentioned therein as the microorganisms of the genus Streptomyces. With this kind of microorganisms, steroids having complicated structures can be efficiently, easily and directly hydroxylated at the 25-position.

DISCLOSURE OF THE INVENTION

The object of the present invention is to provide a biological process for hydroxylating steroids, other than cholesterol, at the 25-position thereof with microorganisms of a genus other than the genus Streptomyces.

The present invention has been completed on the basis of a finding that among various microorganisms, those of the genus Amycolata or Sphingomonas are capable of hydroxylating steroids at the 25-position thereof.

Namely, the present invention provides a biological process for producing steroids hydroxylated at the 25-position thereof, characterized by adding steroids to the cells or culture liquid of a microorganism of the genus Amycolata or Sphingomonas capable of hydroxylating the steroids at the 25-position thereof to convert a hydrogen atom bonded to a carbon atom at the 25-position of each steroid into hydroxyl group.

BEST MODE FOR CARRYING OUT THE INVENTION

The steroid to be hydroxylated in the present invention is any of steroids, other than cholesterol, which have a carbon atom at the 25-position to which hydrogen atom is bonded. In this connection, other carbon atoms of the steroids may be replaced with any elements. For example, the carbon atom at the 22-position may be replaced with an oxygen atom, sulfur atom, nitrogen atom or the like. The steroids may have other substituents such as a lower alkyl group, a cyclic hydrocarbon group, a heterocyclic group such as a triazoline group, or a protected or unprotected hydroxyl group, amino group, hydroxy-lower alkyl group, hydroxy-lower alkoxyl group or acyl group at a position other than the 25-position. They may also have one or more unsaturated bonds in the steroid skeleton and further may have an oxidized epoxy ring obtained by oxidizing the unsaturated bond.

The steroids to be hydroxylated in the present invention are preferably compounds of the following general formula (I):

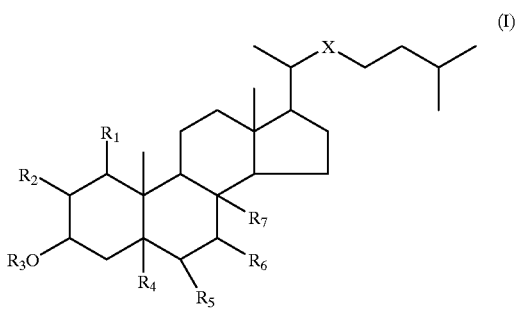

wherein $R_1$ represents a hydrogen atom or a hydroxyl group which may be optionally protected; $R_2$ represents a hydrogen atom or a hydroxy-lower alkoxyl group in which the hydroxyl group may be optionally protected, or $R_1$ and $R_2$ together form a double bond or epoxy ring, $R_3$ represents a hydrogen atom or a protecting group; $R_4$, $R_5$, $R_6$ and $R_7$ each represent a hydrogen atom, one or both couples of $R_4$ and $R_5$, and $R_6$ and $R_7$ form a double bond or, alternatively, $R_5$ and $R_6$ together form a double bond and $R_4$ and $R_7$ are bonded to a dienophile capable of protecting the conjugated double bond; and X represents $CH_2$ or an oxygen atom, with the proviso that when X is $CH_2$, a compound wherein $R_1$, $R_2$, $R_6$ and $R_7$ are hydrogen atom and $R_4$ and $R_5$ together form a double bond is excluded.

The protecting groups in the above formula are, for example, acyl groups such as acetyl, pivaloyl, methoxycarbonyl, benzyloxycarbonyl and p-toluenesulfonyl groups; alkyl groups which may be optionally substituted such as methyl and methoxymethyl groups; and substituted silyl groups such as trimethylsilyl, triethylsilyl and t-butyldimethylsilyl groups. Among them, trimethylsilyl, triethylsilyl and t-butyldimethylsilyl groups are preferred.

As the dienophiles capable of protecting the conjugated double bonds, compounds of the following general formula (II) are used:

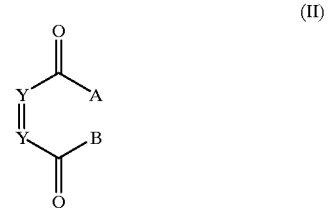

wherein A and B may be the same or different and each represent an alkoxyl group having 1 to 4 carbon atoms, or A and B together form a phenylimino group or p-phenylene group, and Y represents a nitrogen atom or a methine group (=CH—). Among them, 4-phenyl-1,2,4-triazoline-3,5-dion, diethyl maleate, etc. are preferred.

The steroids to be hydroxylated in the present invention include 1α,3β-dihydroxy-5,7-cholestadiene, 2β-(3-hydroxypropyloxy)-1α,3β-dihydroxy-5,7-cholestadiene, 5α,8α-(3,5-dioxo-4-phenyl-1,2,4-triazolizino)-1,6-cholestadiene-3β-ol, 3β-hydroxy-1,5,7-cholestatriene, 1α,2α-epoxy-5α,8α-(3,5-dioxo-4-phenyl-1,2,4-triazolizino)-6-cholesten-3β-ol, 1α,2α-epoxy-3β-hydroxy-5,7-cholestadiene, 20(S)-(3-methylbutyloxy)pregna-5,7-diene-1α,3β-diol, 20(S)-(3-methylbutyloxy)-pregna-5-ene-1α,3β-diol and the like.

According to the process of the present invention, the steroids can be hydroxylated at the 25-position irrespective of the positions or the number of hydroxyl groups in the steroids and, further, they can be hydroxylated at the 25-position irrespective of the positions or the number of double bonds.

The microorganisms of the genus Amycolata capable of hydroxylating the steroids at the 25-position thereof and usable in the present invention include, for example, those of strains of *Amycolata saturnea* A-1246, *Amycolata saturnea* FERM BP-2307 and *Amycolata autotrophica* ATCC 33796. However, microorganisms of any strain are usable so far as they are capable of hydroxylating the steroids at the 25-position thereof. The microorganisms of the genus Sphingomonas include those of, for example, *Sphingomonas parapaucimobilis* IFO 15100.

Microorganisms of any strain of the genus Sphingomonas are usable so far as they are capable of hydroxylating the steroids at the 25-position thereof.

Among them, the strains *Amycolata autotrophica* ATCC 33796 and *Amycolata saturnea* A-1246 are preferred. *Amycolata saturnea* A-1246, which was separated from the soil by the inventors, has the following bacteriological properties:

(1) Morphological Properties

The vegetative hyphae grow well and irregularly branch in a synthetic agar medium or a natural agar medium. No septum is found. The spores are well formed in a glycerol/asparagine agar medium, a starch/inorganic salt agar medium or the like. It is found in the microscopic observation that the sporulation hyphae are simply branched, and the spores are linearly formed. Usually at least three spore linkages are observed, and the chains are long and have the smooth surface in the latter period of the culture. The spores are cylindrical and the size thereof is 0.5 to 0.8×2.5 to 4.3 $\mu$m. The sclerotium, sprangium and flagellate spore were not observed.

(2) Growth in Various Media (30° C.)

(2-1) Sucrose/Nitrate Agar Medium

The growth of the microorganisms on the medium is moderate. The color tone of the back surface of the colony is light brown. The formation of aerial hyphae is medium and they are yellowish white. No soluble pigment is formed.

(2-2) Glucose/Asparagine Agar Medium

The growth of the microorganisms on the medium is relatively poor. The color tone of the back surface of the colony is yellowish white. The formation of aerial hyphae is medium and they are white. No soluble pigment is formed.

(2-3) Glycerol/Asparagine Agar Medium

The growth of the microorganisms on the medium is good. The color tone of the back surface of the colony is light yellow. The formation of aerial hyphae is good and they are white. No soluble pigment is formed.

(2-4) Starch/Inorganic Salt Agar Medium

The growth of the microorganisms on the medium is moderate. The color tone of the back surface of the colony is yellowish white. The formation of aerial hyphae is good and they are white. No soluble pigment is formed.

(2-5) Tyrosine Agar Medium

The growth of the microorganisms on the medium is moderate. The color tone of the back surface of the colony is reddish brown. The formation of aerial hyphae is good and they are yellowish white. A soluble light reddish brown pigment is formed.

(2-6) Nutrient Agar Medium

The growth of the microorganisms on the medium is good. The color tone of the back surface of the colony is light yellow. The formation of aerial hyphae is good and they are white. No soluble pigment is formed.

(2-7) Yeast/Malt Agar Medium

The growth of the microorganisms on the medium is good. The color tone of the back surface of the colony is light yellow. The formation of aerial hyphae is good and they are white. No soluble pigment is formed.

(2-8) Oat Meal Agar Medium

The growth of the microorganisms on the medium is moderate. The color tone of the back surface of the colony is yellowish white. The formation of aerial hyphae is relatively poor and they are white. No soluble pigment is formed.

(2-9) Peptone/Yeast/Iron Agar Medium

The growth of the microorganisms on the medium is moderate. The color tone of the back surface of the colony is light brown. The formation of aerial hyphae is moderate and they are yellowish white. No soluble pigment is formed.

(3) Physiological Properties (3-1) Growth Temperature Range

When the nutrient agar medium is used, a good growth is observed in the temperature range of 20 to 30° C. The microorganisms do not grow at 10° C. or below, or at 40° C. or above.

(3-2) Aerobe or Anaerob: Aerobe (3-3) Gelatin Liquefaction: Positive (3-4) Starch Hydrolysis: Negative (3-5) Coagulation and Peptonization of Skim Milk Powder: Both Negative (3-6) Formation of Melanin-like Pigment: Negative (3-7) Nitrate Reductivity: Negative.

(4) Utilization of Carbon Sources

Various carbon sources were each applied to Pridham-Gottlieb's agar medium and the growth of microorganisms was observed. Carbon sources such as D-glucose, sucrose, D-xylose, inositol, D-mannit and D-fructose were usable, while L-arabinose, L-rhamnose and raffinose were unusable.

(5) Cell wall components were examined by using decomposition products of the whole cells to find that the cell walls belong to type III cell walls according to Lechevalier classification [International Journal of Systematic Bacteriology, vol. 20, pp. 435 to 443 (1970)]. Mycolic acid was not contained therein.

It is apparent from the above-described bacteriological properties that this strain belongs to actinomycetes. By comparing these properties with those of known microorganisms reported in International Journal of Systematic Bacteriology, Vol. 36, pp. 29 to 37 (1986), this strain was substantially identified with *Amycolata saturnea*. From those results, this strain was judged to belong to *Amycolata saturnea*, and named "*Amycolata saturnea*" A-1246. This strain was deposited with the National Institute of Bioscience and Human-Technology of the Agency of Industrial Science and Technology (1-3, Higashi 1-chome, Tsukuba City, Ibaraki Pre f., Japan) to be preserved under FERM BP-5544 on Aug. 7, 1995.

The biological process of the present invention for hydroxylating steroids (other than cholesterol) at the 25-position comprises hydroxylating steroids (other than cholesterol) as the substrate under aerobic conditions in a solution containing microorganisms of the genus Amycolata or Sphingomonas. The cells of the microorganism necessitated for the reaction are produced by inoculating the above-described strain into a nutrient source-containing medium and culturing the microorganisms under aerobic conditions. As a rule, the microorganisms are cultured by an ordinary culture method. Usually, they are preferably cultured under aerobic conditions by, for example, the shaking culture method or spinner culture method under aeration.

As for the medium, any medium is usable so far as it contains nutrient sources for the microorganisms belonging to the genus Amycolata or Sphigomoonas. Various synthetic, semi-synthetic and natural media are usable. As for the composition of the medium, carbon sources such as glucose, maltose, xylose, fructose and sucrose are usable either alone or in combination of them. As the nitrogen sources, organic nitrogen sources such as peptone, meat extract, soybean powder, casein, amino acids, yeast extract and urea; and inorganic nitrogen sources such as sodium nitrate and ammonium sulfate are usable either alone or in combination of them. In addition, salts such as sodium chloride, potassium chloride, calcium carbonate, magnesium sulfate, sodium phosphate, potassium phosphate and cobalt chloride, heavy metal salts and vitamines can also be added if necessary. When the foaming is marked in the course of the culture, a defoaming agent selected from among well known defoaming agents can be properly added to the medium.

The culture conditions can be suitably selected so as to grow the microorganisms of this strain well. Usually, the microorganisms are cultured at a pH of 6 to 7.5 at 28 to 30° C. for about 2 to 8 days. The above-described culture conditions can be suitably altered depending on the kind and characteristics of the microorganisms used and external conditions.

A steroid is added to the reaction solution containing the microorganism cells thus obtained to produce a corresponding steroid having a hydroxyl group at the 25-position. Namely, the culture fluid containing the microorganism cells is directly used or, alternatively, cells are separated from the culture fluid by the centrifugation or filtration after the completion of the culture, and the obtained cells are suspended in a solution to obtain a suspension to be used. The solutions in which the cells can be suspended include the above-described media, and buffer solutions such as tris (hydroxymethyl)aminomethane-acetic acid, tris (hydroxymethyl)aminomethane-hydrochloric acid, sodium succinate, sodium citrate, sodium phosphate and potassium phosphate which are to be used either alone or in the form of a mixture of them. The pH of the buffer solution is preferably 7.0 to 8.5.

The steroid to be used as the substrate is in the form of the powder itself or a solution thereof in a water-soluble organic solvent such as ethanol. The powder or the solution is added to the reaction solution containing the microorganism cells. The amount of the powder or solution is preferably 0.15 to 0.60 mg per ml of the reaction solution. When the amount thereof is larger than 0.60 mg/ml, the conversion velocity is lowered unfavorably. After the addition of the substrate, the shaking or spinning under aeration is conducted at 27 to 31° C. for one to three days, preferably about one day, to conduct the reaction under aerobic conditions, thereby producing the steroid having hydroxyl group at the 25-position thereof.

As described above, steroids having a hydroxyl group at the 25-position thereof can be obtained from steroids by using microorganisms of the genus Amycolata or Sphingomonas. Further, the conversion of the steroids into those having a hydroxyl group at the 25-position thereof can be remarkably increased by introducing a cyclodextrin or a cyclodextrin derivative together with the steroid into the microorganism reaction solution.

The cyclodextrins used in the present invention include β-cyclodextrin and γ-cyclodextrin. The cyclodextrin derivatives include, for example, hydroxypropyl-β-cyclodextrin, maltosyl-β-cyclodextrin, glucosyl-β-cyclodextrin and methylated cyclodextrins. Among them, the methylated cyclodextrins are preferred. The term "methylated cyclodextrins" herein indicates compounds obtained by replacing the hydrogen atom of the hydroxyl group at the 2-, 3- and/or 6-position of cyclodextrin with a methyl group. They include hexakis-(2,6-O-dimethyl)-α-cyclodextrin which is derived from α-cyclodextrin and completely methylated at the 2- and 6-positions, heptakis-(2,6-O-dimethyl)-β-cyclodextrin which is derived from β-cyclodextrin and octakis-(2,6-O-dimethyl)-γ-cyclodextrin which is derived from γ-cyclodextrin; hexakis-(2,3,6-O-trimethyl)-α-cyclodextrin which is derived from α-cyclodextrin and completely methylated at the 2-, 3- and 6-positions, heptakis-(2,3,6-O-trimethyl)-β-cyclodextrin which is derived from β-cyclodextrin and octakis-(2,3,6-O-trimethyl)-γ-cyclodextrin which is derived from γ-cyclodextrin; and partially methylated cyclodextrins (hereinafter referred to as "PMCD") obtained by partially methylating six, seven or eight hydroxyl groups at the 2-,3- and 6-positions. The methylation rate is preferably 50 to 70%, most preferably about 61%. One or more members of the above-described methylated cyclodextrins are selectively used in the present invention. Methylated cyclodextrins derived from β-cyclodextrin are particularly preferred.

The amount of the cyclodextrins or derivatives thereof is preferably 0.1 to 10 mg, more preferably 0.5 to 5 mg, per ml of the reaction solution. When the amount of the cyclodextrins or derivatives thereof is less than 0.1 mg per ml of the reaction solution, the effect of improving the conversion into the steroids having hydroxyl group at the 25-position is insufficient and, on the contrary, when it exceeds 10 mg, the conversion reaction rate is lowered, and the foaming of the reaction solution becomes serious to make the continuation of the microbial reaction difficult.

It is effective to use cyclodextrins together with a surfactant in the present invention. The surfactants are preferably nonionic surfactants such as polyoxyethylene/sorbitan fatty acid esters [such as Tween 80 (a product of Sigma Chemical Company), sorbitan fatty acid esters [such as Span 85 (a product of Sigma Chemical Company)], polyoxyethylene ethers [such as Brij 96 (a product of Sigma Chemical Company)], Triton X-100 (a product of Sigma Chemical Company), nonylphenol [such as Nonipole 45 (a product of Sanyo Chemical Industries, Ltd.) and ethylene oxide/propylene oxide block copolymers [such as Pluronic L-61 (a product of Asahi Denka Kogyo K.K.); and anionic surfactants such as Dislex (a product of Nippon Oils and Fats Co., Ltd.) and Trax (a product of Nippon Oils and Fats Co., Ltd.). The amount of the nonionic surfactant used is preferably about 0.1 to 0.5%

The steroid having hydroxyl group at the 25-position produced by the reaction can be isolated by any of various known methods or a combination of them. The isolation and purification can be conducted by, for example, the extraction with a solvent such as ethyl acetate or n-butanol; column chromatography with silica gel or the like; thin-layer chromatography, liquid-liquid partition chromatography, preparative high-performance liquid chromatography wherein reversed phase column is used; or column chromatography wherein a synthetic adsorbent resin is used. These methods can be employed either solely or in a suitable combination of them, or they can be repeated if necessary.

The following Examples will further illustrate the present invention, which by no means limit the invention, wherein percentages are given by weight unless otherwise stated.

EXAMPLE 1

100 ml of a seed culture medium (hereinafter referred to as "medium A") comprising 1.5% of glucose, 1.5% of Bacto® Soytone (a product of Difco), 0.5% of corn steep liquor (Nihon Shokuhin Kako Co., Ltd.), 0.4% of sodium chloride, 0.2% of calcium carbonate (pH 7.0) and the balance of water was fed into a 500 ml Erlenmeyer flask and sterilized by heating at 120° C. for 20 minutes. 2 ml of frozen yeast culture of Amycolata autotrophica ATCC 33796 was inoculated into the medium. After the shaking culture at 220 rpm (amplitude: 70 mm) at 28° C. for two days, the seed culture fluid was obtained.

Then, 50 ml of a conversion culture medium (hereinafter referred to as "medium B") comprising 2.0% of glucose, 0.2% of yeast extract (Oriental Yeast Co. Ltd.), 0.5% of peptone (Kyokuto Pharmaceutical IND., Co., Ltd.), 1.0% of soybean powder (Esusan Meat; Ajinomoto Co., Ltd.), 0.5% of corn step liquor, 0.04% of potassium secondary phosphate, 0.04% of sodium chloride, 0.2% of calcium carbonate (pH 7.4) and the balance of water was fed into a 250 ml Erlenmeyer flask and sterilized by heating at 120° C. for 20 minutes. 2 ml of the seed culture fluid prepared as described above was inoculated into the medium. After the culture with a rotary shaker at 28° C. for two days, the fluid were poured in test tubes each in an amount of 3 ml.

Partially methylated β-cyclodextrin (methylation rate: 55.8%) was added to each 3 ml culture fluid to obtain a concentration of 0, 0.5 or 1.0% by weight. 250 μg/ml of the following steroid a, b, c or d in the form of a solution in ethanol was added to the resultant mixture. The reaction was conducted in a rotary shaker at 30° C. for 17 hours.

steroid a:

steroid b:

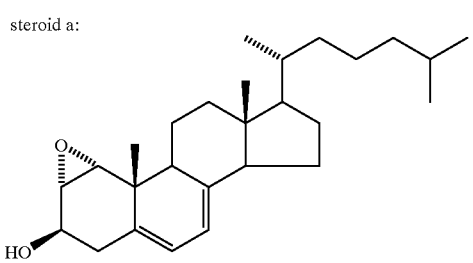
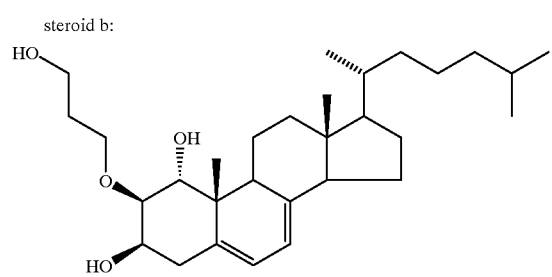

steroid c:
steroid d:

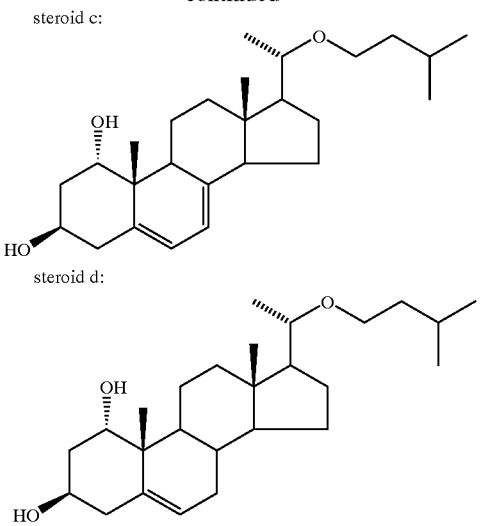

After the completion of the reaction, 1 ml of the obtained culture fluid was fed into a centrifugal precipitation tube having a ground stopper. 9 ml of methanol was added to the fluid, the bottle was tightly stopped and they were mixed for 15 minutes. The liquid mixture was centrifuged at 3,000 rpm for 10 minutes, and the supernatant liquid was analyzed by HPLC. The analysis was conducted by using an HPLC apparatus of L-6000 System (a product of Hitachi, Ltd.), a column of YMC A 503CN (inner diameter: 4.6 mm, the whole length: 250 mm; a product of Yamamura Chemistry) and an eluent comprising acetonitrile and water (55:45) at a flow rate of 1.0 ml/min and at a column temperature of 40° C. The detection was conducted according to the UV absorption at 205 or 265 nm. The quantitative analysis was conducted by the comparison with the areametric values of chemically synthesized standard steroids, a, b, c or d hydrolyzed at the 25 position.

TABLE 1

[Analytical values obtained after 17 hour conversion reaction] (unit: μg/ml)

|  |  | PMCD 0% | PMCD 0.5% | PMCD 1.0% |
|---|---|---|---|---|
| Steroid a | Substrate | 127 | 116 | 7.16 |
|  | 25-OH-steroid | 3.77 | 82.6 | 169 |
| Steroid b | Substrate | 110 | 50.2 | 4.57 |
|  | 25-OH-steroid | 4.05 | 89.8 | 158 |
| Steroid c | Substrate | 0 | 0 | 0 |
|  | 25-OH-steroid | 5.85 | 53.7 | 41.8 |
| Steroid d | Substrate | 0 | 0 | 0 |
|  | 25-OH-steroid | 6.90 | 23.4 | 83.6 |

It is apparent from the above results that according to the present invention, steroids each having hydroxyl group at the 25-position can be efficiently obtained from the steroids and that the rate of the hydroxylation at the 25-position of each steroid is increased in the presence of methylated cyclodextrin.

EXAMPLE 2

The reaction was conducted for six hours in the same manner as that of Example 1 except that steroid a was used as the substrate and that the concentration of PMCD was varied. The quantity of the steroid having hydroxyl group at the 25 position was determined. The results are shown in Table 2.

TABLE 2

[Quantity of 25-hydroxylated steroid after 6 hour reaction]

| PMCD conc. (%) | 0 | 0.25 | 0.50 | 1.0 | 2.0 |
|---|---|---|---|---|---|
| 25-OH-steroid (μg/ml) | 6.7 | 25.1 | 44.5 | 110 | 23.2 |

It is apparent from the above results that the optimum concentration of the methylated cyclodextrin is 1%.

EXAMPLE 3

The reaction was conducted for six hours in the same manner as that of Example 1 except that steroid a was used as the substrate, that the concentration of PMCD was fixed at 1% and the concentration of the substrate was varied. The quantity of the steroid having hydroxyl group at the 25 position was determined. The results are shown in Table 3.

TABLE 3

[Quantity of 25-hydroxylated steroid after 6 hour reaction] (unit: μg/ml)

| Substrate conc. | 65 | 125 | 250 | 500 | 1000 |
|---|---|---|---|---|---|
| 25-OH-steroid | 29.8 | 57.5 | 90.4 | 10.7 | 15.7 |

It is apparent from the above results that the optimum concentration of the steroid is 250 μg/ml.

EXAMPLE 4

The reaction was conducted for 6 hours or 24 hours in the same manner as that of Example 1 except that steroid a was used as the substrate, that 1.0% of various cyclodextrins and derivatives thereof were used and that 0 or 0.2% of Tween 80 was used. The quantity of the produced steroids each having hydroxyl group at the 25-position was determined. The results are shown in Tables 4 and 5.

The cyclodextrins (CD) and derivatives thereof used were as follows:

α-CD, β-CD, γ-CD, hydroxypropyl-β-CD and maltosyl-β-CD.
PMCD-a: partially methylated cyclodextrin (methylation rate: 72.1%)
PMCD-b: partially methylated cyclodextrin (methylation rate: 69.0%)
PMCD-c: partially methylated cyclodextrin (methylation rate: 55.8%)
Mixture of PMCD-1: PMCD-a/PMCD-c=1/2 mixture (methylation rate: 61.2%)
Mixture of PMCD-2: PMCD-a/PMCD-c=2/1 mixture (methylation rate: 66.7%)
DMCD: 2,6-di-O-methyl-β-cyclodextrin (methylation rate: 66.6%)
TMCD: 2,3,6-tri-O-methyl-β-cyclodextrin (methylation rate: 100%)
Mixture of PMCD-3: DMCD/TMCD=1/2 mixture (methylation rate: 88.9%)
Mixture of PMCD-4: PMCD/PMCD=2/1 mixture (methylation rate: 77.7%)

TABLE 4

[Quantity of 25-hydroxylated steroid after 6 hour or 24 hour reaction] (unit: μg/ml)

|  | Reaction for 6 hours | | Reaction for 24 hours | |
|---|---|---|---|---|
| Tween 80 | none | 0.2% | none | 0.2% |
| Without CD | 10.7 | 11.3 | 8.76 | 9.38 |
| α-CD | 11.1 | 8.37 | 2.20 | 3.67 |
| β-CD | 7.53 | 20.0 | 14.3 | 13.0 |
| γ-CD | 13.7 | 34.7 | 17.2 | 9.97 |
| Hydroxypropyl-β-CD | 7.53 | 20.8 | 45.0 | 73.7 |
| Maltosyl-β-CD | 11.1 | 72.4 | 68.4 | 110 |
| PMCD-c | 107 | 88.4 | 160 | 157 |

The effects of all the cyclodextrins (excluding α-cyclodextrin) were observed. The effect of PMCD-c was the most remarkable, and the effects of other cyclodextrins were also improved by the combination with Tween 80 (reaction time: 6 hours). When Tween 80 was used alone, the effect was only slight.

TABLE 5

[Quantity of 25-hydroxylated steroid (unit: μg/ml)]

|  | Methylation rate | Reaction time | |
|---|---|---|---|
|  | (%) | 6 hours | 24 hour |
| No CD |  | 15.3 | 10.7 |
| PMCD-a | 72.1 | 71.4 | 130 |
| PMCD-b | 69.0 | 79.6 | 138 |
| PMCD-c | 55.8 | 89.4 | 144 |
| Mixed PMCD-1 | 61.2 | 115 | 180 |
| Mixed PMCD-2 | 66.7 | 87.7 | 149 |
| DMCD | 66.6 | 54.3 | 147 |
| TMCD | 100 | 43.4 | 108 |
| Mixed PMCD-3 | 88.9 | 50.4 | 126 |
| Mixed PMCD-4 | 77.7 | 44.9 | 128 |

It is apparent from the above results that all the methylated cyclodextrins were effective. In particular, the highest average methylation rate of 61% was obtained when each of the methylated cyclodextrins was used.

EXAMPLE 5

The reaction was conducted for 6 hours or 24 hours in the same manner as in Example 1 except that steroid a was used and various microorganisms were used in the absence or presence of 1% PMCD, and the quantity of the steroid having hydroxyl group at the 25-position was determined. The results are shown in Table 6.

The microoorganisms used were as follows:

*Amycolata saturnea* A-1246 (FERM BP 5544)
*Amycolata autotrophica* (ATCC 33796)
*Streptomyces roseosprous* (FERM BP 1574)
*Sphingomonas parapaucimobilis* (IFO 15100)
Streptomyces sp. HB-103 (FERM BP 4318)

TABLE 6

[Quantity of 25-hydroxylated steroid (unit: μg/ml)]

|  | 6 Hour reaction | | 24 hour reaction | |
| --- | --- | --- | --- | --- |
|  | No CD | 1% PMCD | No CD | 1% PMCD |
| Amycolata saturnea A-1246 | 10.7 | 107 | 8.76 | 160 |
| Amycolata autotrophica ATCC 33796 | 9.31 | 111 | 0 | 177 |
| Streptomyses roseosprous FERM BP 1574 | 2.65 | 4.29 | 0 | 10.4 |
| Sphingomonas prapaucimobilis IFO 15100 | 2.28 | 2.04 | 1.72 | 1.71 |
| Streptomyces sp. HB-103 | 5.50 | 30.5 | 5.21 | 90.5 |

EXAMPLE 6

100 ml of medium A was fed into a 500 ml Erlenmeyer flask. After stopping with a cotton stopper, it was sterilized with steam at 121° C. for 20 minutes. After cooling, one platinum wire loop of *Amycolata autotrophica* ATCC 33796 was inoculated thereinto, and the shaking culture was conducted at 28° C. at 210 rpm for three days. 50 ml of medium B which further contained 1.0% of PMCD (methylation rate: 55.8%) was fed into each of four 250 ml Erlenmeyer flasks, the flasks were each stopped with a cotton stopper and sterilized at 121° C. under a high pressure for 20 minutes. 1.0 ml of the culture fluid obtained with medium A as described above was poured into each flask under sterile conditions and then cultured at 28° C. at 220 rpm (amplitude: 70 mm) for two days. As the control, the same procedure as that described above was repeated except that PMCD-free medium B was used. A solution of 25 mg of steroid a in 1 ml of ethanol was added to each culture fluid and the culture was continued under the above-described conditions for 24 hours. A solution of 25 mg of steroid a in 1 ml of ethanol was added to the culture fluid and the culture was continued under the above-described conditions for 24 hours (concentration of steroid a added: 1 g/l). After the completion of the reaction, 1 ml of the obtained culture fluid was fed into a centrifugal precipitation tube having a ground stopper. 9 ml of methanol was added to the fluid, the bottle was tightly stopped and they were mixed for 15 minutes. The liquid mixture was centrifuged at 3,000 rpm for 10 minutes, and the supernatant liquid was analyzed by HPLC. The analysis was conducted by using an HPLC apparatus of L-6000 System (a product of Hitachi, Ltd.), a column of YMC A 503CN (inner diameter: 4.6 mm, the whole length: 250 mm; a product of Yamamura Chemistry) and an eluent comprising acetonitrile and water (55:45) at a flow rate of 1.0 ml/min and at a column temperature of 40° C. The detection was conducted according to the UV absorption at 205 or 265 nm. The quantitative analysis was conducted by the comparison with the areametric values of chemically synthesized steroid a hydrolyzed at the 25 position. As a result, the formation of 780 mg/l of steroid a hydroxylated at the 25-position was recognized. When PMCD was not added to the medium, the amount of steroid a hydroxylated at the 25-position was 9.1 mg/l.

200 ml of the reaction fluid obtained in the PMCD-containing medium B was centrifuged at 3,000 rpm for 10 minutes to obtain a supernatant liquid, which was passed through an Amberlite XAD-7 column (inner diameter: 30 mm, length: 140 mm; a product of Organo) to adsorb steroid a and also steroid a hydroxylated at the 25-position. After washing the column with water and 50% methanol followed by the elution with 100% methanol, the effluent was concentrated to dryness under reduced pressure.

The dry concentrate thus obtained was dissolved in a small amount of n-hexane/ethyl acetate (3:1) and the solution was adsorbed at the top of a column filled with 50 g of Wako Gel C-300 (a product of Wako Pure Chemical Industries, Ltd.) and n-hexane/ethyl acetate (3:1). 500 ml of n-hexane/ethyl acetate (3:1) was passed through the column. After the elution with n-hexane/ethyl acetate (3:2), the effluent fraction was analyzed by HPLC, and a fraction of steroid a hydroxylated at the 25-position was concentrated to dryness under reduced pressure.

Then the dry product was separated by HPLC under the following conditions: column: Inertsil Prep-ODS (20×250 mm; a product of GL Science Co., Ltd.), eluent: 90% methanol, flow rate: 10 ml/min, and detection: UV absorption at 265 nm. As a result, 97 mg of steroid a hydroxylated at the 25-position was obtained. The structure of the isolated product was analyzed according to the nuclear magnetic resonance, infrared absorption and mass spectrum to confirm that it was the steroid a hydroxylated at the 25-position.

The properties of the obtained product hydroxylated at the 25-position were as follows:

m.p.: 169 to 171° C.

$[\alpha]_D$: −16.0 (c0.5, MeOH, 21.8° C.)

FAB-MS(M/Z): 414(M+H)$^+$ (Matrix: m-nitrobenzyl alcohol) (calculated: 413: $C_{27}H_{41}O_3$)

IR$\nu_{max}$ cm$^{-1}$: 3382, 2959, 2870, 1449, 1377, 1267, 1151, 1047, 930

UV$\lambda_{max}$ nm (ε): 260(8860 sh), 269(12300), 280(12750), 291(7210)

$^1$H-NMR(CDCl$_3$) δ (ppm): 5.72(1H, d, J=4 Hz), 5.40(1H, m), 3.91(1H, m), 3.33(1H, d, J=4 Hz), 3.05(1H, d, J=4 Hz), 2.4 to 2.5(2H, m), 2.24(1H, t, J=11 Hz), 2.1 to 2.15(1H, m), 2.01(1H, d, J=5 Hz), 1.88 to 1.95(2H, m), 1.78 to 1.85(2H, m), 1.66 to 1.71(1H, m), 1.22 to 1.5(11H, m), 1.22(6H, s), 1.05(3H, s), 0.97(3H, d, J=7 Hz), 0.64(3H, s)

$^{13}$C-NMR(CDCl$_3$) δ (ppm): 141.5(s), 133.7(s), 122.0(d), 115.9(d), 71.1(s), 67.2(d), 60.9(d), 60.2(d), 55.7(d), 54.5(d), 44.4(t), 42.7(s), 39.7(d), 38.8(t), 38.4(s), 36.9(t), 36.4(t), 36.1(d), 29.4(q), 29.2(q), 28.0(t), 23.0(t), 20.8(t), 20.6(t), 18.8(q), 15.2(q), 11.9(q)

EXAMPLE 7

The reaction was conducted for six hours in the same manner as that of Example 2, and the steroids having hydroxyl group at the 25-position were determined. The results are shown in Table 7.

TABLE 7

[Quantity of 25-hydroxylated steroid after 6 hour reaction]

| PMCD concentration (%) | 0 | 0.25 | 0.5 | 1.0 | 2.0 |
|---|---|---|---|---|---|
| 25-OH-steroid (μg/ml) | 4.0 | 7.5 | 24 | 8.0 | 7.5 |

It is apparent from the above-described results that the optimum concentration of the partially methylated cyclodextrin is 0.5%.

EXAMPLE 8

The reaction was conducted for six hours in the same manner as that of Example 3 except that steroid b was used as the substrate. The quantity of the steroid having hydroxyl group at the 25-position was determined. The results are shown in Table 8.

TABLE 8

[Quantity of 25-hydroxylated steroid after 6 hour reaction]

| Substrate conc. (%) | 65 | 125 | 250 | 500 | 1000 |
|---|---|---|---|---|---|
| 25-OH-steroid (μg/ml) | 10.5 | 17.4 | 23.2 | 8.50 | 3.45 |

It is apparent from the above results that the optimum concentration of the steroid is 250 μg/ml. Example 9 Synthesis of steroid b hydroxylated at the 25-position:

200 ml of a culture fluid (to be divided and fed into four flasks) was obtained by culturing *Amycolata autotrophica* ATCC 33796 in PMCD-containing culture B in the same manner as that of Example 6. A solution of 25 mg of steroid b in 1 ml of ethanol was added to the culture fluid in each flask and the culture was continued under the above-described conditions for 24 hours. A solution of 25 mg of steroid b in 1 ml of ethanol was added to the culture fluid and the culture was continued under the above-described conditions for 24 hours (concentration of steroid b added: 1 g/l). As a result, the formation of 778 mg/l of steroid b hydroxylated at the 25-position was accumulated in the PMCD-containing medium B. When PMCD was not added to the medium, the amount of steroid b hydroxylated at the 25-position was 4.0 mg/l.

200 ml of the reaction fluid obtained in the PMCD-containing medium B was centrifuged at 3,000 rpm for 10 minutes to obtain a supernatant liquid, which was passed through an Amberlite XSD-7 column (inner diameter: 30 mm, length: 140 mm; a product of Organo) to adsorb steroid b and also steroid b hydroxylated at the 25-position. After washing the column with water and then with 50% methanol followed by the elution with 100% methanol, the effluent was concentrated to dryness under reduced pressure.

The dry concentrate thus obtained was dissolved in a small amount of dichloromethane/ethanol (19:1) and the solution was adsorbed at the top of a column filled with 50 g of Wako Gel C-300 (a product of Wako Pure Chemical Industries, Ltd.) and dichloromethane/ethanol (19:1). After the elution with dichloromethane/ethanol (19:1), the effluent fraction was analyzed by HPLC, and a fraction of steroid b hydroxylated at the 25-position was concentrated to dryness under reduced pressure to obtain 103 mg of steroid b hydroxylated at the 25-position.

m.p.: 155 to 157° C. (crystallized from chloroform)

$[\alpha]_D$: 44.6 (c 0.5, MeOH, 22° C.)

FAB-MS(m/z): 490(M)$^+$ (matrix: m-nitrobenzyl alcohol, Positive mode) 489(M–H) (matrix: m-nitrobenzyl alcohol Native mode (Calculated:490:$C_{30}H_{50}O_6$)

IR$\nu_{max}$ cm$^{-1}$: 3385, 2938, 2870, 1468, 1379, 1136, 1096, 1055, 910

UV$\lambda_{max}$ nm (ε): 262(6570 sh), 272(9400), 282(10010), 294(5850)

$^1$H-NMR(CDCl$_3$) δ (ppm): 5.71 (1H, m, J=5.5, 2.2 Hz), 5.40 (1H, m, J=5.5, 2.6 Hz), 3.6 to 4.0(7H, m), 2.5 to 2.7 (2H, m), 2.32 (1H, dd, J=14, 5 Hz), 2.10 (1H, m), 1.23 to 2.0 (22H, m), 1.22 (6H, s), 1.07 (3H, s), 0.96 (3H, d, J=6.6 Hz), 0.63 (3H,s)

$^{13}$C-NMR(CDCl$_3$) δ (ppm): 141.0(s), 136.1(s), 124.6(d), 115.4(d), 82.3(d), 71.8(d), 71.1(s), 68.9(t), 67.0(d), 60.8(t), 55.9(d), 54.6(d), 44.4(t), 43.1(s),41.8(s), 39.2(t), 38.7(d), 36.4(t), 36.1(d), 35.2(t), 32.3(t), 29.4(q),29.2(q), 28.1(t), 23.0(t), 21.1(t), 20.8(t), 18.8(q), 15.9(q), 11.9(q)

What is claimed is:

1. A biological process for producing steroids hydroxylated at the 25-position thereof, which comprises adding steroids (excluding cholesterol) to the cells or culture liquid of a microorganism of the genus Amycolata or Sphingomonas capable of hydroxylating the steroids at the 25-position thereof to convert a hydrogen atom bonded to a carbon atom at the 25-position of each steroid into hydroxyl group.

2. The process of claim 1 wherein the steroid is a compound selected from the group consisting of 1α,3β-dihydroxy-5,7-cholestadiene, 2β-(3-hydroxypropyloxy)-1α, 3β-dihydroxy-5,7-cholestadiene, 5α,8α-(3,5-dioxo-4-phenyl-1,2,4-triazolizino)-1,6-cholestadiene-3β-ol, 3β-hydroxy-1,5,7-cholestatriene, 1α,2α-epoxy-5α,8α-(3,5-dioxo-4-phenyl-1,2,4-triazolizino)-6-cholesten-3β-ol,1α, 2α-epoxy-3β-hydroxy-5,7-cholestadiene, and 20(S)-(3-methylbutyloxy)-pregna-5-ene-1 α,3β-diol.

3. The process of claim 2, wherein the steroid is 1α,3β-dihydroxy-5,7-cholestadiene.

4. The process of claim 2, wherein the steroid is 2β-(3-hydroxypropyloxy)-1α, 3β-dihydroxy-5,7-cholestadiene.

5. The process of claim 2, wherein the steroid is 5α,8α-(3,5-dioxo-4-phenyl-1,2,4-triazolizino)-1,6-cholestadiene-3β-ol.

6. The process of claim 2, wherein the steroid is 3β-hydroxy-1,5,7-cholestatriene.

7. The process of claim 2, wherein the steroid is 1α,2α-epoxy-5α,8α-(3,5-dioxo-4-phenyl-1,2,4-triazolizino)-6-cholesten-3β-ol.

8. The process of claim 2, wherein the steroid is 1α,2α-epoxy-3β-hydroxy-5,7-cholestadiene.

9. The process of claim 2, wherein the steroid is 20(S)-(3-methylbutyloxy)-pregna-5-ene-1α, 3β-diol.

10. The process of claim 1, wherein the microorganisms of the genus Amycolata are *Amycolata saturnea*.

11. The process of claim 1, wherein the microorganisms of the genus Amycolata are *Amycolata saturnea* A-1246.

12. The process of claim 1, wherein the microorganisms of the genus Amycolata are *Amycolata autotrophica*.

13. The process of claim 1, wherein the microorganisms of the genus Amycolata are *Amycolata autotrophica* ATCC 33796.

14. The process of claim 1, wherein the microorganisms of the genus Sphingomonas are *Sphingomonas parapaucimobilis*.

15. The process of claim 1, wherein the microorganisms of the genus Sphingomonas are *Sphingomonas parapaucimobilis* IFO 15100.

16. The process of any of claims 1, which is conducted in the presence of a cyclodextrin or a cyclodextrin derivative.

17. The process of claim 16, wherein the cyclodextrin is β- or γ-cyclodextrin.

18. The process of claim 16, wherein the cyclodextrin derivative is a methylated cyclodextrin.

19. The process of claim 18, wherein the methylation rate of the methylated cyclodextrin is 50 to 70%.

20. The process of claim 18, wherein the methylation rate of the methylated cyclodextrin is about 61%.

21. The process of any of claim 16, wherein the amount of the cyclodextrin or the cyclodextrin derivative is 0.1 to 10 mg per ml of the reaction solution.

22. The process of claim 21, wherein the amount of the cyclodex-trin or the cyclodextrin derivative is 0.5 to 5 mg per ml of the reaction solution.

23. The process of any of claim 16, wherein the reaction is conducted in the presence of a surfactant.

24. The process of claim 23, wherein the surfactant is a nonionic surfactant.

25. The process of claim 24, wherein the nonionic surfactant is at least one surfactant selected from the group consisting of polyoxyethylene/sorbitan fatty acid esters, sorbitan/fatty acid esters, polyoxyethylene ethers, Triton X-100, nonylphenol and ethylene oxide/propylene oxide block copolymers.

26. The process of claim 24, wherein the nonionic surfactant is used in an amount of 0.1 to 0.5%.

* * * * *